United States Patent
Benn

(10) Patent No.: US 9,750,678 B2
(45) Date of Patent: Sep. 5, 2017

(54) HAIR COLORING COMPOSITIONS COMPRISING LATEX POLYMERS

(71) Applicant: L'OREAL, Paris (FR)

(72) Inventor: Mark Benn, Union, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/577,809

(22) Filed: Dec. 19, 2014

(65) Prior Publication Data

US 2016/0175233 A1 Jun. 23, 2016

(51) Int. Cl.
| | | |
|---|---|---|
| A61Q 5/10 | (2006.01) | |
| A61K 8/81 | (2006.01) | |
| A61K 8/41 | (2006.01) | |
| A61K 8/49 | (2006.01) | |
| A61K 8/87 | (2006.01) | |

(52) U.S. Cl.
CPC ............. *A61K 8/8152* (2013.01); *A61K 8/41* (2013.01); *A61K 8/4973* (2013.01); *A61K 8/87* (2013.01); *A61Q 5/10* (2013.01); *A61K 2800/30* (2013.01); *A61K 2800/594* (2013.01); *A61K 2800/882* (2013.01)

(58) Field of Classification Search
CPC .......... A61Q 5/10; A61K 8/41; A61K 8/4973; A61K 2800/43; A61K 2800/594; A61K 2800/882
USPC ........................................................... 8/405
See application file for complete search history.

(56) References Cited

U.S. PATENT DOCUMENTS

| | | |
|---|---|---|
| 3,110,695 A | 11/1963 | Ceresa |
| 3,304,273 A | 2/1967 | Stamberger |
| 3,383,351 A | 5/1968 | Paul |
| 3,412,054 A | 11/1968 | Milligan et al. |
| 3,523,095 A | 8/1970 | James et al. |
| 3,915,921 A | 10/1975 | Schlatzer, Jr. |
| 4,003,699 A | 1/1977 | Rose et al. |
| RE30,199 E | 1/1980 | Rose et al. |
| 4,509,949 A | 4/1985 | Huang et al. |
| 4,644,030 A | 2/1987 | Loewrigkeit et al. |
| 4,710,374 A | 12/1987 | Grollier et al. |
| 4,798,721 A | 1/1989 | Yahagi et al. |
| 4,985,239 A | 1/1991 | Yahagi et al. |
| 5,061,289 A | 10/1991 | Clausen et al. |
| 5,085,859 A | 2/1992 | Halloran et al. |
| 5,156,911 A | 10/1992 | Stewart |
| 5,173,526 A | 12/1992 | Vijayendran et al. |
| 5,221,534 A | 6/1993 | DesLauriers et al. |
| 5,380,340 A | 1/1995 | Neunhoeffer et al. |
| 5,441,728 A | 8/1995 | Tsaur et al. |
| 5,534,267 A | 7/1996 | Neunhoeffer et al. |
| 5,565,216 A | 10/1996 | Cowsar et al. |
| 5,618,523 A | 4/1997 | Zysman et al. |
| 5,637,291 A | 6/1997 | Bara et al. |
| 5,663,366 A | 9/1997 | Neunhoeffer et al. |
| 5,679,327 A | 10/1997 | Darkwa et al. |
| 5,708,151 A | 1/1998 | Moeckli |
| 5,753,215 A | 5/1998 | Mougin et al. |
| 5,766,576 A | 6/1998 | Loewe et al. |
| 5,932,194 A | 8/1999 | Plessix et al. |
| 6,013,682 A | 1/2000 | Dalle et al. |
| 6,099,592 A | 8/2000 | Vidal et al. |
| 6,110,451 A | 8/2000 | Matz et al. |
| 6,120,778 A | 9/2000 | Simonnet |
| 6,126,929 A | 10/2000 | Mougin |
| 6,126,948 A | 10/2000 | Simonnet et al. |
| 6,165,446 A | 12/2000 | Samain et al. |
| 6,214,328 B1 | 4/2001 | Chang et al. |
| 6,284,003 B1 | 9/2001 | Rose et al. |
| 6,338,741 B1 | 1/2002 | Vidal et al. |
| 6,399,050 B1 | 6/2002 | Pasquet et al. |
| 6,464,990 B2 | 10/2002 | Simonnet et al. |
| 6,482,394 B1 | 11/2002 | Schehlmann et al. |
| 6,585,965 B1 | 7/2003 | Carballada et al. |
| 6,592,633 B2 | 7/2003 | Lang et al. |
| 6,613,315 B1 | 9/2003 | Dupuis |
| 6,645,258 B2 | 11/2003 | Vidal et al. |
| 6,703,028 B1 | 3/2004 | Samain et al. |
| 6,726,916 B1 | 4/2004 | Ramin |
| 6,730,789 B1 | 5/2004 | Birault et al. |

(Continued)

FOREIGN PATENT DOCUMENTS

| | | |
|---|---|---|
| DE | 1152536 B | 8/1963 |
| DE | 2359399 A1 | 6/1975 |

(Continued)

OTHER PUBLICATIONS

Co-pending U.S. Appl. No. 14/576,639, Siliu Tan et al., "Hair Styling Compositions Comprising Latex Polymers," filed Dec. 19, 2014.
Co-pending U.S. Appl. No. 14/578,074, Siliu Tan et al., "Compositions and Methods for Hair," filed Dec. 19, 2014.
Co-pending U.S. Appl. No. 14/577,740, Christine Shin et al., "Hair Cosmetic Composition Containing Latex Polymers and a Silicone-Organic Polymer Compound," filed Dec. 19, 2014.
Co-pending U.S. Appl. No. 14/577,579, Siliu Tan et al., "Hair Styling Compositions Comprising Latex Polymers and Wax Dispersions," filed Dec. 19, 2014.
Co-pending U.S. Appl. No. 14/586,105, Siliu Tan et al., "Compositions and Methods for Hair," filed Dec. 30, 2014.
Co-pending U.S. Appl. No. 14/578,122, Christine Shin, "Hair Cosmetic Composition Containing a Polyurethane Latex Polymer and a Silicone Organic Polymer Compound," filed Dec. 19, 2014.
Co-pending U.S. Appl. No. 13/931,329; Siliu Tan et al., "Compositions and Methods for Treating Hair," filed Jun. 28, 2013.
Co-pending U.S. Appl. No. 13/931,187; Siliu Tan et al., "Compositions and Methods for Treating Hair," filed Jun. 28, 2013.

(Continued)

*Primary Examiner* — Eisa Elhilo
(74) *Attorney, Agent, or Firm* — The Marbury Law Group, PLLC

(57) ABSTRACT

Disclosed is color base composition for coloring keratin fibers comprising: at least two latex polymers independently selected from acrylate latex polymers and polyurethane latex polymers; at least one alkalizing agent; at least one oxidative dye precursor; at least one organic solvent; and water; wherein the at least two latex polymers are partially or fully neutralized; and wherein the at least two latex polymers are present in a combined amount ranging from about 0.2% to about 2.5% by weight, relative to the weight of the composition.

26 Claims, No Drawings

(56) References Cited

U.S. PATENT DOCUMENTS

| | | | |
|---|---|---|---|
| 7,211,244 B2 | 5/2007 | Auguste et | |
| 7,651,693 B2 | 1/2010 | Merlau et al. | |
| 7,740,832 B1 | 6/2010 | Rollat-Corvol et al. | |
| 7,785,613 B2 | 8/2010 | Collin et al. | |
| 7,993,632 B2 | 8/2011 | Lezer et al. | |
| 8,343,238 B1 | 1/2013 | Lopez et al. | |
| 8,398,961 B2 | 3/2013 | Kaplan et al. | |
| 8,691,200 B2 | 4/2014 | Vilbert | |
| 8,865,147 B2 | 10/2014 | Rizk et al. | |
| 2002/0007521 A1 | 1/2002 | Lang et al. | |
| 2002/0010970 A1* | 1/2002 | Cottard et al. | 8/405 |
| 2002/0050013 A1 | 5/2002 | Vidal et al. | |
| 2002/0055562 A1 | 5/2002 | Butuc | |
| 2002/0198328 A1 | 12/2002 | L'Alloret | |
| 2003/0019051 A9 | 1/2003 | Vidal et al. | |
| 2003/0026815 A1 | 2/2003 | Scott et al. | |
| 2003/0044440 A1 | 3/2003 | Toumi | |
| 2003/0053976 A1 | 3/2003 | Tournilhac et al. | |
| 2003/0059377 A1 | 3/2003 | Riley | |
| 2003/0059388 A1 | 3/2003 | Auguste et al. | |
| 2003/0064045 A1 | 4/2003 | Tournilhac et al. | |
| 2003/0103927 A1 | 6/2003 | Maubru | |
| 2003/0138465 A9 | 7/2003 | Douin et al. | |
| 2003/0147832 A1 | 8/2003 | L'Alloret | |
| 2003/0161804 A1 | 8/2003 | Perron et al. | |
| 2004/0071646 A1 | 4/2004 | Pataut et al. | |
| 2004/0096474 A1 | 5/2004 | Merlau et al. | |
| 2004/0214913 A1 | 10/2004 | L'Alloret | |
| 2005/0008605 A1 | 1/2005 | L'Alloret | |
| 2005/0025736 A1 | 2/2005 | Jachowicz et al. | |
| 2005/0048016 A1 | 3/2005 | Lebreton et al. | |
| 2005/0053568 A1 | 3/2005 | Aubrun-Sonneville et al. | |
| 2005/0065253 A1 | 3/2005 | Collin et al. | |
| 2005/0089490 A1 | 4/2005 | Jachowicz et al. | |
| 2006/0115446 A1 | 6/2006 | Rollat-Corvol et al. | |
| 2006/0134043 A1 | 6/2006 | Nakamura | |
| 2006/0182702 A1 | 8/2006 | Lazzeri et al. | |
| 2006/0292095 A1 | 12/2006 | Biatry et al. | |
| 2007/0031361 A1 | 2/2007 | Herrmann et al. | |
| 2007/0190008 A1 | 8/2007 | Campain et al. | |
| 2007/0224140 A1 | 9/2007 | Quadir et al. | |
| 2007/0286833 A1 | 12/2007 | Keller et al. | |
| 2008/0138307 A1 | 6/2008 | Bazemore et al. | |
| 2008/0175808 A1 | 7/2008 | Pavel | |
| 2008/0305064 A1 | 12/2008 | Bui et al. | |
| 2009/0035335 A1 | 2/2009 | Marotta et al. | |
| 2009/0060858 A1 | 3/2009 | Schwarzwaelder et al. | |
| 2009/0074695 A1 | 3/2009 | Mahe et al. | |
| 2009/0280076 A1 | 11/2009 | Yoshida et al. | |
| 2009/0297467 A1 | 12/2009 | Laurent et al. | |
| 2009/0317432 A1 | 12/2009 | Kergosien | |
| 2010/0028284 A1 | 2/2010 | Atis et al. | |
| 2010/0119467 A1 | 5/2010 | Dumousseaux et al. | |
| 2010/0189678 A1 | 7/2010 | Knappe et al. | |
| 2010/0278770 A1 | 11/2010 | Arditty et al. | |
| 2011/0014139 A1 | 1/2011 | Viala et al. | |
| 2011/0015279 A1 | 1/2011 | Doerr et al. | |
| 2011/0097289 A1 | 4/2011 | Viala et al. | |
| 2011/0097293 A1 | 4/2011 | Grey et al. | |
| 2011/0150802 A1* | 6/2011 | Bui et al. | 424/63 |
| 2011/0150807 A1 | 6/2011 | Bui et al. | |
| 2012/0247500 A1 | 10/2012 | Plos et al. | |
| 2012/0308496 A1 | 12/2012 | Viala et al. | |
| 2013/0084256 A1 | 4/2013 | Li et al. | |
| 2013/0167863 A1 | 7/2013 | Schmelz et al. | |
| 2013/0171084 A1* | 7/2013 | Kawaratani et al. | 424/64 |
| 2013/0284198 A1 | 10/2013 | Rizk et al. | |
| 2014/0105845 A1 | 4/2014 | Bui et al. | |
| 2014/0105945 A1 | 4/2014 | Bui et al. | |
| 2014/0186270 A1 | 7/2014 | Suleiman et al. | |

FOREIGN PATENT DOCUMENTS

| | | |
|---|---|---|
| DE | 2364398 A1 | 10/1975 |
| DE | 3843892 A1 | 6/1990 |
| DE | 4133957 A1 | 4/1993 |
| DE | 19543988 A1 | 5/1997 |
| DE | 102009054516 A1 | 6/2011 |
| EP | 0216479 A1 | 4/1987 |
| EP | 0692237 A1 | 1/1996 |
| EP | 0714954 A2 | 6/1996 |
| EP | 0770375 A1 | 5/1997 |
| EP | 0847752 A1 | 6/1998 |
| EP | 0874017 A2 | 10/1998 |
| EP | 0898958 A1 | 3/1999 |
| EP | 0898960 A1 | 3/1999 |
| EP | 1082953 A1 | 3/2001 |
| EP | 1291051 A2 | 3/2003 |
| EP | 1466588 A1 | 10/2004 |
| EP | 1652509 A2 | 5/2006 |
| EP | 2356981 A1 | 8/2011 |
| EP | 2570192 A1 | 3/2013 |
| FR | 2633940 B3 | 7/1991 |
| FR | 2733749 A1 | 11/1996 |
| FR | 2774899 A1 | 8/1999 |
| FR | 2801308 A1 | 5/2001 |
| FR | 2834458 A1 | 7/2003 |
| FR | 2856923 A1 | 1/2005 |
| FR | 2889943 A1 | 3/2007 |
| FR | 2898050 A1 | 9/2007 |
| FR | 2961103 A1 | 12/2011 |
| FR | 2968978 A1 | 6/2012 |
| GB | 1026978 A | 4/1966 |
| GB | 1040452 A | 8/1966 |
| GB | 1153196 A | 5/1969 |
| JP | H021956 A | 1/1990 |
| JP | H05163124 A | 6/1993 |
| KR | 20100105168 A | 9/2010 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 0119333 A1 | 3/2001 |
| WO | 2005100444 A1 | 10/2005 |
| WO | 2007099269 A2 | 9/2007 |
| WO | 2010133658 A2 | 11/2010 |
| WO | 2011056332 A1 | 5/2011 |
| WO | 2011069786 A2 | 6/2011 |
| WO | 2011137338 A2 | 11/2011 |
| WO | 2012049146 A2 | 4/2012 |
| WO | 2012/072774 A1 | 6/2012 |
| WO | 2013059106 A1 | 4/2013 |
| WO | 2013074210 A1 | 5/2013 |
| WO | 2013092378 A1 | 6/2013 |
| WO | 2013092379 A1 | 6/2013 |
| WO | 2013092380 A1 | 6/2013 |
| WO | 2013092381 A1 | 6/2013 |
| WO | 2013092382 A1 | 6/2013 |
| WO | 2013092562 A1 | 6/2013 |
| WO | 2013092779 A2 | 6/2013 |
| WO | 2013092788 A1 | 6/2013 |
| WO | 2014001390 A1 | 1/2014 |
| WO | 2014001391 A1 | 1/2014 |
| WO | 2014/058856 A1 | 4/2014 |
| WO | 2014071354 A1 | 5/2014 |
| WO | 2014124066 A1 | 8/2014 |

OTHER PUBLICATIONS

Co-pending U.S. Appl. No. 13/931,204; Siliu Tan et al., "Compositions and Methods for Treating Hair," filed Jun. 28, 2013.

Co-pending U.S. Appl. No. 13/931,222; Siliu Tan et al., "Compositions and Methods for Treating Hair," filed Jun. 28, 2013.

Co-pending U.S. Appl. No. 13/931,238; Siliu Tan et al., "Compositions and Methods for Treating Hair," filed Jun. 28, 2013.

Co-pending U.S. Appl. No. 13/931,248; Siliu Tan et al., "Compositions and Methods for Treating Hair," filed Jun. 28, 2013.

Co-pending U.S. Appl. No. 13/931,260; Siliu Tan et al., "Compositions and Methods for Treating Hair," filed Jun. 28, 2013.

Co-pending U.S. Appl. No. 13/931,276; Siliu Tan et al., "Compositions and Methods for Treating Hair," filed Jun. 28, 2013.

(56) References Cited

OTHER PUBLICATIONS

Co-pending U.S. Appl. No. 13/931,288; Siliu Tan et al., "Compositions and Methods for Treating Hair," filed Jun. 28, 2013.
Co-pending U.S. Appl. No. 13/931,298; Siliu Tan et al., "Compositions and Methods for Treating Hair," filed Jun. 28, 2013.
Co-pending U.S. Appl. No. 13/931,312; Siliu Tan et al., "Compositions and Methods for Treating Hair," filed Jun. 28, 2013.
English language abstract for EP 0770375 (May 2, 1997).
English language abstract for EP0898960 (Mar. 3, 1999).
English language abstract for EP1082953 (Mar. 14, 2001).
English language abstract for FR2633940 (Jul. 12, 1991).
English language abstract for FR2898050 (Sep. 7, 2007).
English language abstract for FR2968978 (Jun. 22, 2012).
English language Abstract of FR2834458 (Jul. 11, 2003).
Galgoci, Ernest C., et al., "Solvent-Free Urethane-Acrylic Hybrid Polymers for Coatings," JCT Coatings Tech, 2 (13), Feb. 2005, pp. 28-36.
International Search Report for Application No. PCT/US2014/044036, mailed Oct. 21, 2014, 3 pages.
International Search Report for Application No. PCT/US2014/044377, mailed Oct. 31, 2014, 3 pages.
International Search Report for Application No. PCT/US2014/044557, mailed Oct. 13, 2014, 3 pages.
International Search Report for Application No. PCT/US2014/044587, mailed Oct. 31, 2014, 3 pages.
International Search Report for Application No. PCT/US2014/044610, mailed Oct. 31, 2014, 4 pages.
Jachowicz, J., et al., "Mechanical Analysis of Elasticity and Flexibility of Virgin and Polymer-Treated Hair Fiber Assemblies," J. Cosmet. Sci., 53, Nov./Dec. 2002, pp. 345-361.
Non-Final Office Action for U.S. Appl. No. 13/931,187, dated Feb. 13, 2015.
Non-Final Office Action for U.S. Appl. No. 13/931,204, dated Feb. 20, 2015.
Non-Final Office Action for U.S. Appl. No. 13/931,238, dated Feb. 13, 2015.
Non-Final Office Action for U.S. Appl. No. 13/931,248, dated Feb. 20, 2015.
Non-Final Office Action for U.S. Appl. No. 13/931,260, dated Feb. 20, 2015.
Non-Final Office Action for U.S. Appl. No. 13/931,276, dated Feb. 17, 2015.
Non-Final Office Action for U.S. Appl. No. 13/931,288, dated Feb. 18, 2015.
Non-Final Office Action for U.S. Appl. No. 13/931,298, dated Feb. 20, 2015.
Non-Final Office Action for U.S. Appl. No. 13/931,312, dated Feb. 18, 2015.
Non-Final Office Action for U.S. Appl. No. 13/931,329, dated Feb. 13, 2015.
Polyquats As Conditioning Agents, 2009. Retrieved from the Internet.
English language abstract for DE 102009054516 (Jun. 16, 2011).
English language abstract for EP 0847752 (Jun. 17, 1998).
English language abstract for FR 2961103 (Dec. 16, 2011).
English language abstract for JP H05-163124 (Jun. 29, 1993).
English language abstract for KR 20100105168 (Sep. 29, 2010).
Final Office Action for co-pending U.S. Appl. No. 13/931,187 (Jul. 20, 2015).
Non-Final Office Action for co-pending U.S. Appl. No. 13/931,222 (Apr. 7, 2015).
Final Office Action for co-pending U.S. Appl. No. 13/931,222 (Jul. 28, 2015).
English language abstract for JP H021956 (Jan. 8, 1990).
International Search Report and Written Opinion for copending Application No. PCT/US2015/066818, mailed Feb. 26, 2016.
Extended European Search Report for counterpart EP Application No. 14818460.9, mailed Nov. 21, 2016.
Extended European Search Report for counterpart EP Application No. 14817786.8, mailed Oct. 14, 2016.
Extended European Search Report for counterpart EP Application No. 14817057.4, mailed Nov. 2, 2016.
Extended European Search Report for counterpart EP Application No. 14818467.4, mailed Nov. 9, 2016.

* cited by examiner

HAIR COLORING COMPOSITIONS COMPRISING LATEX POLYMERS

FIELD OF THE INVENTION

The present application relates to a color base composition containing latex polymers, alkalizing agent, oxidative dye precursor, organic solvent, and water and to a method of coloring hair.

BACKGROUND OF THE INVENTION

It is known that consumers desire to use cosmetic and personal care compositions that enhance the appearance of keratin fibers such as hair by changing the color of the hair and/or by imparting various properties to hair such as shine and conditioning. The process of changing the color of hair can involve either depositing an artificial color onto the hair which provides a different shade or color to the hair or lifting the color of the hair, such as for example, from a dark brown shade to a medium brown or a light brown shade.

Conventional hair coloring products include permanent hair dyeing products, also known as oxidation dyeing, which use the combination of compositions containing oxidative dye precursors, also known as primary intermediates or oxidation bases, and oxidizing products containing oxidizing agents such as peroxide and persulfate compounds, under alkaline pH conditions in the vast majority of cases. In general, the oxidation dye precursors comprise oxidation bases chosen from ortho- or para-phenylenediamines, ortho- or para-aminophenols, and heterocyclic compounds. These oxidation bases are colorless or weakly colored compounds, which, when combined with oxidizing products, can give access to colored species via a process of oxidative condensation.

The shades obtained with these oxidation bases may often be varied by combining them with at least one coupler, these couplers being chosen, for example, from aromatic meta-diamines, meta-aminophenols, meta-diphenols, and certain heterocyclic compounds, such as indole compounds. The variety of molecules used as oxidation bases and couplers can allow a wide range of colors to be obtained.

The oxidizing agent employed in permanent dyeing compositions may degrade the melanin of the hair, which, depending on the nature of the oxidizing agent present, may lead to less pronounced lightening of the fibers. Thus, for relatively weak lightening, the at least one oxidizing agent may be, for example, hydrogen peroxide. When more substantial lightening is desired, peroxygenated salts, such as persulfates, may be used in the presence of hydrogen peroxide.

Hair coloring compositions typically contain aqueous ammonia as an alkalizing agent and for activating the oxidizing agent. These alkalizing agents also cause the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. However, the use of ammonia may affect the user, not only because of the undesirable odor of ammonia, but because it may also pose greater risks of intolerance, for instance, irritation of the scalp and stinging.

The option of replacing all or at least some of the aqueous ammonia with at least one other standard alkalizing agent frequently does not lead to compositions that are as efficient as those based on aqueous ammonia, for example since these alkalizing agents may not afford sufficient lightening of pigmented fibers in the presence of an oxidizing agent.

Thus, there is a need in the art for improved and/or alternate dyeing processes performed in the presence of at least one oxidizing agent, which do not have at least one of the drawbacks of the existing processes.

In order to improve the performance of such hair coloring compositions, the use of new and additional ingredients and novel combinations of ingredients are continuously sought; however, the choice of ingredients could pose difficulties insofar as they must improve the dyeing/lifting capability of the composition without being detrimental to other properties of the composition such as its application, rheology or viscosity properties, stability and/or resulting into more disadvantages such as increased damage or a less healthy look to the hair. At the same time, ingredients in hair coloring compositions such as oxidative hair color which can be alkaline or acidic have to remain stable and active. For example, while the use of polymeric material in cosmetic compositions may be useful due to certain properties such as film forming and coating properties, their use in acidic or alkaline compositions pose challenges since the polymeric material may not be stable or remain active. Moreover, polymers that may coat or form a film on the hair may also adversely impact the deposit of color on the hair.

In addition, certain hair coloring compositions such as permanent hair dyes are generally employed on hair as final mixtures of two part systems composed of color base compositions containing the dyes and oxidizer/developer compositions containing the oxidizing agent. Thus, selection of ingredients and their amounts in such systems are critical not only for the composition properties of each of the color base and oxidizer compositions, but also for the dyeing, cosmetic, and application properties of the final mixtures.

It is also important to provide hair coloring compositions with various types of consistency, such that the compositions can be provided in the form of a liquid emulsion, such as a liquid-lotion, liquid-gel, liquid-cream, or a cream emulsion, such as a thick cream or gel-cream, or a foam or mousse wherein the liquid emulsion form has a thinner consistency than the cream emulsion form and is typically packaged in a bottle. The liquid emulsion form is generally employed when the entire head of hair is to be colored or when only one color is desired since the dye composition spreads easily, allowing for greater coverage while the cream emulsion form can be employed for dyeing the entire head of hair and for highlighting or lightening only certain sections of the hair.

Thus, the objective of the present invention is to obtain novel compositions for oxidatively dyeing the hair. Another objective of the invention is to obtain oxidative hair coloring compositions that provide very good color deposit and at the same time, have a unique, non-drip consistency or rheology and yet spread easily on the hair while imparting other advantages to the hair such as conditioning, a healthy appearance, shine and less damage to the hair. It has now been surprisingly and unexpectedly discovered that by providing a color base composition comprising at least one two latex polymers which are partially or fully neutralized and are selected from acrylate latex polymers and polyurethane latex polymers, at least one alkalizing agent, at least one oxidative dye precursor, at least one organic solvent and water wherein the at least two latex polymers are present in a combined amount by weight of a specific range, relative to the weight of the composition, it is possible to achieve these objectives. It is also possible for the composition of the invention to impart shaping and/or styling benefits to the hair, for example to make it easier to curl or style the hair.

SUMMARY OF THE INVENTION

The present invention is directed to a color base composition for coloring keratin fibers containing:
(a) at least two latex polymers independently selected from acrylate latex polymers and polyurethane latex polymers;
(b) at least one alkalizing agent;
(c) at least one oxidative dye precursor;
(d) at least one organic solvent; and
(e) water;
wherein the at least two latex polymers are partially or fully neutralized;
wherein the at least two latex polymers are present in a combined amount ranging from about 0.2% to about 2.5% by weight, relative to the weight of the composition.

The present invention is also drawn to a composition for altering the color of hair, wherein the composition is formed from the combination of the above-disclosed color base composition with a composition containing at least one oxidizing agent.

The present invention is also drawn to methods of coloring hair, comprising applying onto the hair, the composition for altering the color of hair formed from the combination of the above-disclosed color base composition with a composition containing at least one oxidizing agent.

The present invention is also drawn to methods of coloring hair, comprising combining the above-disclosed color base composition with a composition containing at least one oxidizing agent in order to form a composition for altering the color of hair and applying said composition for altering the color of hair onto hair.

It has been surprisingly and unexpectedly discovered that the use of the at least two latex polymers of the present invention in a combined amount within a specific % range in combination with an alkalizing agent, oxidative dye precursors, organic solvents, and water provided a color base composition which when combined with a composition containing at least one oxidizing agent resulted in very good color deposit.

It has been surprisingly and unexpectedly discovered that the alkaline color base composition of the invention was stable and did not exhibit phase separation when latex polymers are present in the compositions.

DETAILED DESCRIPTION

As used herein, the expression "at least one" means one or more and thus includes individual components as well as mixtures/combinations.

It is also to be understood that, as used herein the terms "the," "a," or "an," mean "at least one," are understood to encompass the plural as well as the singular and should not be limited to "only one" unless explicitly indicated to the contrary. Thus, for example, the use of "an acid" is intended to mean at least one acid.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratin fiber" as used herein, includes, but is not limited to hair, such as hair on the human head and eyelashes.

As used herein, the term "carbonated" or "carbonation" is understood to mean the combination of a bicarbonate compound and at least one acid.

"Film former" or "film forming polymer" as used herein means a polymer or resin that leaves a film on the substrate to which it is applied, for example, after a solvent accompanying the film former has evaporated, absorbed into and/or dissipated on the substrate. These terms may also refer to a polymer capable, by itself or in the presence of an auxiliary film forming polymer, of forming a continuous or a discontinuous film that adheres to a support and especially to keratin substrates such as keratin fibers or hair.

"Film former" or "film forming polymer" as used herein may also be referred to as fixing polymers when such polymers are employed to fix or keep keratin fibers in a particular configuration or shape or arrangement.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

As used herein, the terms "applying a composition onto keratin fibers" and "applying a composition onto hair" and variations of these phrases are intended to mean contacting the fibers or hair, with at least one of the compositions of the invention, in any manner.

The term "treat" (and its grammatical variations) as used herein refers to the application of the compositions of the present invention onto keratin fibers such as hair.

The compositions and methods of the present invention can comprise, consist of, or consist essentially of the essential elements and limitations of the invention described herein, as well as any additional or optional ingredients, components, or limitations described herein or otherwise useful.

Unless otherwise specified herein, all percentages and ratios of components are by weight, relative to the total weight of the final composition.

In an embodiment, the present invention relates to a color base composition for coloring keratin fibers containing:
(a) at least two latex polymers independently selected from acrylate latex polymers and polyurethane latex polymers;

(b) at least one alkalizing agent;
(c) at least one oxidative dye precursor;
(d) at least one organic solvent; and
(e) water;
wherein the at least two latex polymers are partially or fully neutralized;
wherein the at least two latex polymers are present in a combined amount ranging from about 1% to about 2.3% by weight, relative to the weight of the composition.

In some embodiments, a certain amount of the alkalizing agent is used to neutralize the at least two latex polymers.

The at least two latex polymers in the above-described compositions may be chosen from Acrylates copolymer (ACULYN 33 or LUVIFLES® SOFT or DAITOSOL 5000AD), Acrylates/Hydroxyesters Acrylates Copolymer (Acudyne 180), Polyacrylate-2 Crosspolymer (Fixate Superhold™), Styrene/Acrylic copolymer (Neocryl® A-1120), Acrylates/Ethylhexyl Acrylate Copolymer (DAITOSOL 5000SJ), aliphatic polyurethane, Polyurethane-34 (BAYCUSAN® C1000), Polyurethane-34 (BAYCUSAN® C1001), Polyurethane-32 (BAYCUSAN® C1003), Polyurethane-35 (BAYCUSAN® C1004), Polyurethane-48 (BAYCUSAN® C1008), Polyurethane-1 (Luviset® P.U.R), Polycarbamyl Polyglycon Ester (Neorez® R989), and mixtures thereof.

In another embodiment, the at least two latex polymers in the above-described compositions are acrylate latex polymers.

In some embodiments, the acrylate latex polymers are selected from acrylates copolymer, acrylates/hydroxyesters acrylates copolymer, Polyacrylate-2 Crosspolymer, Styrene/Acrylic copolymer, Acrylates/Ethylhexyl Acrylate Copolymer, and mixtures thereof.

Preferably, the acrylate latex polymers are selected from acrylates copolymer and acrylates/hydroxyesters acrylates copolymer.

In some embodiments, the above-described compositions contain not more than two latex polymers. In certain embodiments, the two latex polymers are selected from acrylates copolymer and acrylates/hydroxyesters acrylates copolymer.

In other embodiments, the at least two latex polymers in the above-described compositions are polyurethane latex polymers.

In some embodiments, the polyurethane latex polymers are selected from aliphatic polyurethane, Polyurethane-34, Polyurethane-32, Polyurethane-35, Polyurethane-48, Polyurethane-1, Polycarbamyl Polyglycon Ester, and mixtures thereof.

In yet other embodiments, the at least two latex polymers in the above-described compositions comprise acrylate latex polymers and polyurethane latex polymers.

In other embodiments, the at least one organic solvent in the above-described compositions is chosen from volatile and non-volatile organic solvents.

Thus, in an embodiment, the present invention relates to a color base composition for coloring keratin fibers containing:
(a) at least two latex polymers selected from acrylate latex polymers;
(b) at least one alkalizing agent;
(c) at least one oxidative dye precursor;
(d) at least one organic solvent; and
(e) water;
wherein the at least two latex polymers are partially or fully neutralized;
wherein the at least two latex polymers are present in a combined amount ranging from about 1.5% to about 2.1% by weight, relative to the weight of the composition The above-described color base compositions may further comprise additional or auxiliary agents suitable for use in hair coloring compositions such as direct dyes, pigments, oils other than the at least one organic solvent, waxes, surfactants, rheology modifiers and viscosity modifying/thickening agents, conditioning agents, sequestering agents, emulsifiers, humectants, plasticizers, coalescers, fillers, preserving agents, fragrances, antioxidants, wetting agents, spreading agents, dispersants, sunscreens, and mixtures thereof.

The above-described color base compositions are capable of being mixed with an oxidizing composition containing at least oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture. The resulting composition comprising the color base composition and the oxidizing composition is used for dyeing or coloring hair.

Latex Polymers

According to various exemplary embodiments of the invention, the at least two latex polymers, may, independently, be chosen from acrylate and polyurethane polymers.

In certain embodiments, when the first latex polymer is chosen from acrylate polymers, the second latex polymer is chosen from polyurethane polymers; and when the first latex polymer is chosen from polyurethane polymers, the second latex polymer is chosen from acrylate polymers.

In other embodiments, the at least two latex polymers are chosen from acrylate latex polymers.

In yet other embodiments, the at least two latex polymers are chosen from polyurethane latex polymers.

In various embodiments, the at least two latex polymers may be identified as polymer A and polymer B. Compositions according to certain embodiments may comprise at least one polymer A and at least one polymer B, wherein both polymer A and polymer B are film-forming polymers.

In at least certain exemplary and non-limiting embodiments, latex polymers A and B may be chosen such that polymer A comprises at least one latex polymer that is a relatively soft, flexible latex polymer, and polymer B comprises at least one latex polymer that is a relatively hard, brittle polymer, although such characteristics are not required.

In at least other certain exemplary and non-limiting embodiments, latex polymers A and B may be chosen such that polymer A comprises at least one latex polymer that is a relatively hard, brittle polymer and polymer B comprises at least one latex polymer that is a relatively soft, flexible latex polymer, although such characteristics are not required.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By "at least two latex polymers," it is contemplated that more than two latex polymers may be chosen. Thus, for example, in various embodiments, the composition may comprise polymers A and/or B, which are latex film-forming polymers, and the composition may also comprise at least one latex polymer C that is a non-film-forming polymer; and so on.

In further embodiments, the composition comprises exactly two latex polymers.

In other embodiments, the composition comprises exactly two latex polymers at least one of which is a film-forming polymer.

According to additional embodiments, the composition comprises exactly two latex polymers, both of which are film-forming polymers.

In yet further embodiments, the composition comprises at least two latex polymers, one or both of which are film-forming polymers, but does not comprise any additional film-forming polymers.

In at least certain embodiments of the invention, the at least two latex polymers are provided in the form of aqueous dispersions prior to formulating the compositions of the invention. In various embodiments, the aqueous dispersions may be obtained through an emulsion polymerization of monomers wherein the resulting latex polymers have a particle size lower than about 1 micron. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers are produced from condensation reactions between monomers and subsequently dispersed in an aqueous medium.

Thus, the latex polymers may, in various exemplary embodiments, exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the invention, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex particles according to the invention may have an average diameter ranging up to about 1000 nm, such as from about 50 nm to about 800 nm, or from about 100 nm to about 500 nm. Such particle sizes may be measured with a laser granulometer (e.g. Brookhaven B190).

In various embodiments, the latex polymers may, independently, be neutralized or partially neutralized. In exemplary embodiments where the latex polymers are neutralized or partially neutralized, the particle size may be, for example, greater than about 800 nm. In at least certain embodiments, the particulate form of the latex polymers is retained in the dispersion medium.

In further embodiments, the latex polymers may be chosen from uncharged and charged latex polymers. Thus, the latex polymers may, according to various exemplary embodiments, be chosen from nonionic latex polymers, cationic latex polymers, and anionic latex polymers.

In some embodiments, the polyurethane latex polymer dispersions of the present invention may be employed in the compositions of the present invention, in an amount, of from about 0.5 to about 3% by weight, preferably from about 0.6 to about 2.5% by weight, more preferably from about 0.7 to about 2% by weight, including all ranges and subranges there-between, relative to the weight of the composition.

In some embodiments, the individual latex polymers of the present invention may be employed in the compositions of the present invention, in an amount of from about 0.1 to about 1.5% by weight, or from about 0.5 to about 1.4% by weight, or from about 0.7 to about 1.3% by weight, or from about 0.84 to about 1.26% by weight, or from about 0.84 to about 1.235% by weight, including all ranges and subranges there-between, relative to the weight of the composition.

In various embodiments according to the invention, the at least two latex polymers may be present, in a combined amount ranging from about 0.2% to about 2.5% by weight, or from about 0.75 to about 2.4%, or from about 1% to about 2.3% by weight, preferably from about 1.1% to about 2.2% by weight, or more preferably from about 1.2% to about 2.1% by weight, or even more preferably from about 1.5% to about 2.075% by weight, including all ranges and subranges there-between, relative to the weight of the composition. These weights are on a dry weight basis.

In other embodiments, the at least two latex polymers may be present, in a combined amount of about 0.75%, about 0.8%, about 0.84%, about 0.85%, about 0.9%, about 1%, about 1.1%, about 1.2%, about 1.3%, about 1.4%, or about 1.5%, about 1.6%, about 1.7%, about 1.8%, about 1.9%, about 2%, or about 2.075%, about 2.1% by weight, relative to the weight of the composition. These weights are on a dry weight basis.

As non-limiting examples of latex polymers that may be used, mention may be made, independently, of acrylate latex polymers and polyurethane latex polymers.

By way of non-limiting example only, the latex polymers may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth) acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth) acrylic, cyclohexyl (meth)acrylic, isohexyl (meth)acrylic, heptyl (meth)acrylic, isoheptyl (meth)acrylic, octyl (meth) acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth) acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth) acrylate, isopropyl oxide (meth)acrylate, butyl oxide (meth) acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth) acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth) acrylate, N,N-diethyleaminoethyl (meth)acrylate, and N,N, N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl (meth) acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, -methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

Silicone acrylic polymers may also optionally be used as vinyl polymer in at least one exemplary and non-limiting embodiment.

In at least certain, non-limiting exemplary embodiments, acrylic latex polymers may be chosen from aqueous dispersions of Methacrylic Acid/Ethyl Acrylate copolymer (INCI: Acrylates Copolymer, such as LUVIFLEX® Soft by BASF), PEG/PPG-23/6 Dimethicone Citraconate/C10-30 Alkyl PEG-25 Methacrylate/Acrylic Acid/Methacrylic Acid/Ethyl Acrylate/Tri methylolpropane PEG-15 Triacrylate copolymer (INCI: Polyacrylate-2 Crosspolymer, such as FIXATE SUPERHOLD™ by Lubrizol), Styrene/Acrylic copolymer (such as NEOCRYL® A-1120, DSM), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as DAITOSOL 5000AD, Daito Kasei Kogyo), Vinyl Acetate Acrylic Ester Copolymer (INCI name: Acrylates/VA Copolymer, such as VINYSOL 2140, Daido Chemical) and Acrylates Copolymers, such as those known under the tradename ACULYN™ 33 (Dow Chemical), under the tradename LUVIMER® MAE (BASF), or under the tradename BALANCE CR (AKZO NOBEL).

In yet further exemplary and non-limiting embodiments, the latex polymers may be chosen from polyurethane latex polymers, such as aqueous polyurethane dispersions comprising the reaction products of (i), (ii), and/or (iii), defined below.

Reaction product (i) may be any prepolymer according to the formula:

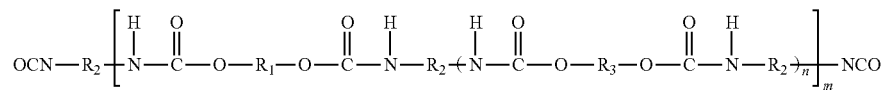

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the invention.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecane¬dioic, 1,3-cyclohexanedicarboxylic, 1,4-cyclo¬hexane-dicarboxylic, 2,5-norboranedicarboxylic, diglycolic, thiodipropionic, 2,5-naphthalene-dicarboxylic, 2,6-naphthalene¬dicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the invention. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythio¬ether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexane¬diol. Polyacetals useful according to various non-limiting embodiments of the invention can also be prepared by polymerization of cyclic acetals.

Optional polyhydroxy polyesteramides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanato¬methyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxy¬cyclo¬hexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylohbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

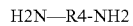

H2N—R4-NH2 wherein R4 is chosen from alkylene or alkylene oxide radicals, said radicals not being substituted with ionic or potentially ionic groups.

Reaction product (ii) may optionally be chosen from alkylene diamines, such as hydrazine, ethylene¬diamine, propylenediamine, 1,4-butylenediamine and piperazine; and alkylene oxide diamines such as dipropylamine diethylene glycol (DPA-DEG available from Tomah Products, Milton, Wis.), 2-methyl-1,5-pentanediamine (Dytec A from DuPont), hexanediamine, isophorone¬diamine, and 4,4-methylenedi(cyclohexylamine), and the DPA-series of ether amines available from Tomah Products, Milton, Wis., including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

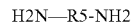

H2N—R5-NH2 wherein R5 is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such latexes include, but are not limited to, aqueous polyurethane dispersions comprising a reaction product of a prepolymer, such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989, INCI name: Polycarbamyl Polyglycon Ester).

In at least certain embodiments, the at least two latex polymers may be chosen from polyacrylic latex, polyacrylate latex, polystyrene latex, polyester latex, polyamide latex, polyurea latex, polyurethrane latex, epoxy resin latex, and their copolymers.

In various embodiments according to the invention, it may be possible to choose a polymer that comprises both acrylate and polyurethane parts at the molecular level.

In certain embodiments, the latex polymers of the present invention are preferably chosen from Acrylates copolymer (copolymer of two or more monomers consisting of acrylic acid, methacrylic acid or one of their simple esters), commercially available as an aqueous dispersion under the tradename ACULYN 33™ (DOW CHEMICAL) and Acrylates/Hydroxyesters Acrylates Copolymer, commercially available as an aqueous dispersion under the tradename ACUDYNE 180 (DOW CHEMICAL).

Alkalizing Agents

The alkalizing agent of the present invention may be chosen from organic amines, organic amine salts, ammonium salts, inorganic bases, and hydroxide base compounds.

The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical.

Organic amines may also be chosen from alkanolamines such as mono-, di- or trialkanolamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

The organic amines correspond to the formula (IV):

$$\text{Rx}\diagdown\text{N}-\text{W}-\text{N}\diagup\text{Rz} \atop \text{Ry}\diagup \qquad \diagdown\text{Rt} \qquad (IV)$$

wherein W is chosen from C1-C6 alkylene residues optionally substituted with a hydroxyl group or a C1-C6 alkyl radical; Rx, Ry, Rz and Rt, which may be identical or different, are chosen from a hydrogen atom, C1-C6 alkyl radicals, C1-C6 hydroxyalkyl radicals, and C1-C6 aminoalkyl radicals.

Examples of such amines that may be mentioned include but not limited to: 1,3-diaminopropane, 1,3-diamino-2-propanol, spermine, and spermidine.

In some embodiments, the organic amines are chosen from amino acids.

As non-limiting examples, the amino acids that may be used may be of natural or synthetic origin, in L, D, or racemic form, and comprise at least one acid function chosen from, for instance, carboxylic acid, sulfonic acid, phosphonic acid, and phosphoric acid functions. The amino acids may be in their neutral or ionic form.

Further as non-limiting examples, the amino acids may be chosen from basic amino acids comprising an additional amine function optionally included in a ring or in a ureido function.

Such basic amino acids may be chosen from those corresponding to formula (A) below:

$$\text{R}-\text{CH}_2-\text{CH}\diagup\text{NH}_2 \atop \diagdown\text{CO}_2\text{H} \qquad (A)$$

wherein R is a group chosen from:

$$\underset{\text{NH}}{\overset{}{\diagdown}}\text{N};\quad -(\text{CH}_2)_3\text{NH}_2;\quad -(\text{CH}_2)_2\text{NH}_2;$$

$$-(\text{CH}_2)_2\text{NHCONH}_2;\quad -(\text{CH}_2)_2\text{NH}-\underset{\underset{\text{NH}}{\|}}{\text{C}}-\text{NH}_2$$

The compounds corresponding to formula (A) may be chosen from histidine, lysine, arginine, ornithine, and citrulline.

Amino acids that may be used in the present disclosure include but not limited to: aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

In some embodiments, the organic amines are chosen from basic amino acids. The amino acids may be chosen from, for instance, arginine, lysine and histidine, or mixtures thereof.

In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole.

In some embodiments, the organic amines are chosen from amino acid dipeptides. Amino acid dipeptides that may be used in the present disclosure include but not limited to: carnosine, anserine, and baleine.

In some embodiments, the organic amines are chosen from compounds comprising a guanidine function. Organic amines of this type that may be used in the present disclosure include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

As a non-limiting example, the organic amines are chosen from alkanolamines. For example, the organic amines are chosen from ethanolamine, triethanoloamine, 2-amino-2-methyl-1-propanol (amino methyl propanol), or preferably from 2-amino-2-methyl-1-propanol and monoethanolamine, or mixtures thereof. Further as an example, the organic amine is monoethanolamine.

The alkalizing agent may be an organic amine in salt form. The term "organic amine salt," as used herein, means organic or mineral salts of an organic amine as described above.

As a non-limiting example, the organic salts may be chosen from the salts of organic acids, such as citrates, lactates, glycolates, gluconates, acetates, propionates, fumarates, oxalates and tartrates.

Further as a non-limiting example, the mineral salts may be chosen from hydrohalides (for example hydrochlorides), carbonates, hydrogen carbonates, sulfates, hydrogen phosphates, and phosphates.

The ammonium salts that may be used according to the present disclosure may be chosen from the following acid salts: carbonate, bicarbonate. For instance, the salt is the carbonate, such as ammonium carbonate.

The inorganic bases that may be used may be chosen from alkali metal phosphates and carbonates such as, for example, sodium phosphate, potassium phosphate, sodium carbonate, sodium bicarbonate, potassium carbonate, potassium bicarbonate, and their derivatives.

The inorganic bases may also include alkali metals of carboxylates such as, for example, sodium acetate, potassium acetate, sodium citrate, and potassium citrate, and their derivatives.

The hydroxide base compounds can be chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

According to at least one embodiment, the alkalizing agent is chosen from alkali metal carbonates, alkali metal phosphate, organic amines, hydroxide base compounds, and derivatives thereof.

According to at least one embodiment, the alkalizing agent is chosen from aminomethyl propanol, aminomethyl propanediol, triisopropanol amine) sodium hydroxide, potassium hydroxide, ammonium hydroxide, dimethylstearylamine, dimethyl/tallowamine lysine, ornithine, arginine, monoethanolamine, triethanolamine, calcium hydroxide, calcium bicarbonate, sodium bicarbonate, and mixtures thereof.

According to one embodiment, the alkalizing agent is chosen from at least one organic amine such as at least one alkanolamine. A particularly preferred alkanolamine is ethanolamine (also known as monoethanolamine or MEA).

Another particularly preferred alkalizing agent is aminomethyl propanol.

The at least one alkalizing agent of the present invention may be employed in an amount of from about 0.01% to about 30% by weight, such as from about 0.1% to about 20% by weight, and further such as from about 0.2% to about 10% by weight, or such as from about 0.3% to about 10% by weight, based on the total weight of the color base composition of the present invention.

The amount of the alkalizing agent in the color base composition can be such that the pH of the composition can be in the acidic (pH below 7), neutral or alkaline range pH above 7).

In certain embodiments, a portion of the alkalizing agent is used to neutralize the at least two latex polymers before or after the polymers are added during the process of making the color base composition. In such a case, the alkalizing agent may also be called a neutralizing agent.

According to at least one embodiment, the compositions or compositions for altering the color of keratin fibers of the present invention contain a small amount of ammonia, or is substantially free of ammonia.

According to another embodiment, the compositions or compositions for altering the color of keratin fibers of the present invention contain ammonia/ammonium hydroxide in an amount such that it is used as the alkalizing agent in the compositions.

Oxidative Dye Precursors

The color base composition of the present invention comprises at least one oxidative dye precursors. The color base composition of the present invention may further comprise direct dyes, pigments, and mixtures thereof.

The oxidation dyes are generally chosen from one or more oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N, N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (β-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present invention are selected from 3-aminopyrazolo-[1,5-a]-pyridines and preferably substituted on carbon atom 2 by:
(a) one (di)(C1-C6)(alkyl)amino group wherein said alkyl group can be substituted by at least one hydroxy, amino, imidazolium group;
(b) one heterocycloalkyl group containing from 5 to 7 members chain, and from 1 to 3 heteroatomes, potentially cationic, potentially substituted by one or more (C1-C6)alkyl, such as di(C1-C4)alkylpiperazinium; or
(c) one (C1-C6)alkoxy potentially substituted by one or more hydroxy groups such as -hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the invention may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethyl-aminobenzene, sesamol, 1-β- hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, 6-hydroxyindoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methyl-pyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present invention.

The coupler(s), if they are present, each advantageously represent from 0.001% to 10% by weight relative to the total weight of the composition, and preferably from 0.005% to 5% by weight relative to the total weight of the compositions of the present invention.

Compositions according to the invention may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Preferably direct dyes are cationic direct dyes. Mention may be made of the hydrazono cationic dyes of formulas (Va) and (V'a), the azo cationic dyes (VIa) and (VI'a) and the diazo cationic dyes (VIIa) below:

Het+-C(Ra)=N—N(Rb)—Ar,An–     (Va)

Het+-N(Ra)—N=C(Rb)—Ar,An–     (V'a)

Het+-N=N—Ar,An–     (VIa)

Ar+—N=N—Ar",An–     (VI'a) and

Het+-N=N—Ar'—N=N—Ar,An–     (VIIa)

in which formulas (Va), (V'a), (VIa), (VI'a) and (VIIa):
Het+ represents a cationic heteroaryl radical, preferably bearing an endocyclic cationic charge, such as imidazolium, indolium or pyridinium, optionally substituted preferentially with one or more (C1-C8) alkyl groups such as methyl;
Ar+ representing an aryl radical, such as phenyl or naphthyl, bearing an exocyclic cationic charge, preferentially ammonium, particularly tri(C1-C8)alkylammonium such as trimethylammonium;
Ar represents an aryl group, especially phenyl, which is optionally substituted, preferentially with one or more electron-donating groups such as i) optionally substituted (C1-C8)alkyl, ii) optionally substituted (C1-C8) alkoxy, iii) (di)(C1-C8)(alkyl)amino optionally substituted on the alkyl group(s) with a hydroxyl group, iv) aryl(C1-C8)alkylamino, v) optionally substituted N—(C1-C8)alkyl-N-aryl(C1-C8)alkylamino or alternatively Ar represents a julolidine group;
Ar' is an optionally substituted divalent (hetero)arylene group such as phenylene, particularly para-phenylene, or naphthalene, which are optionally substituted, preferentially with one or more groups (C1-C8)alkyl, hydroxyl or (C1-C8)alkoxy;
Ar" is an optionally substituted (hetero)aryl group such as phenyl or pyrazolyl, which are optionally substituted, preferentially with one or more groups (C1-C8)alkyl, hydroxyl, (di)(C1-C8)(alkyl)amino, (C1-C8)alkoxy or phenyl;
Ra and Rb, which may be identical or different, represent a hydrogen atom or a group (C1-C8)alkyl, which is optionally substituted, preferentially with a hydroxyl group;
or alternatively the substituent Ra with a substituent of Het+ and/or Rb with a substituent of Ar and/or Ra with Rb form, together with the atoms that bear them, a (hetero)cycloalkyl;
particularly, Ra and Rb represent a hydrogen atom or a group (C1-C4)alkyl, which is optionally substituted with a hydroxyl group;
An– represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954.

Preferentially, the cationic part is derived from the following derivatives:

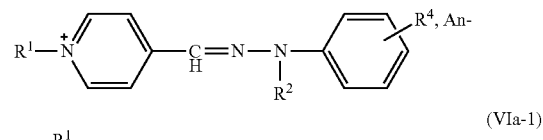

(Va-1)

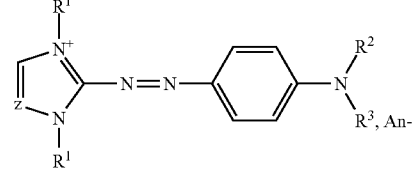

(VIa-1)

formulae (V-1) and (VI-1) with:
R1 representing a (C1-C4) alkyl group such as methyl;
R2 and R3, which are identical or different, represent a hydrogen atom or a (C1-C4)alkyl group, such as methyl; and
R4 represents a hydrogen atom or an electron-donating group such as optionally substituted (C1-C8)alkyl, optionally substituted (C1-C8)alkoxy, or (di)(C1-C8) (alkyl)amino optionally substituted on the alkyl group(s) with a hydroxyl group; particularly, R4 is a hydrogen atom,
Z represents a CH group or a nitrogen atom, preferentially CH;
An– represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

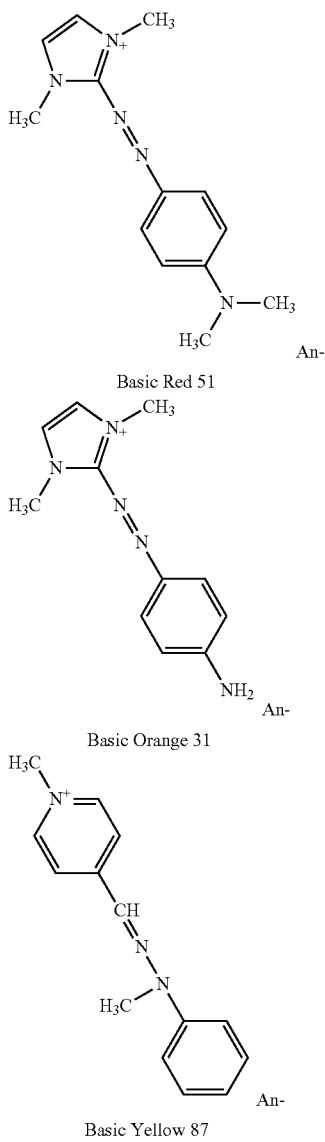

Basic Red 51

Basic Orange 31

Basic Yellow 87

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present invention.

Organic Solvents

The compositions of the present invention comprise at least one organic solvent.

Suitable organic solvents may be chosen from volatile and nonvolatile organic solvents.

Suitable organic solvents are typically C1-C4 lower alcohols, glycols, polyols, polyol ethers, hydrocarbons, and oils.

Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL DPnB.

Suitable organic solvents also include synthetic oils and hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, polybutene, hydrogenated polyisobutene, hydrogenated polydecene, polydecene, squalene, petrolatum and isoparaffins, silicone oils, fluoro oils and mixtures, thereof.

The term "hydrocarbon-based oil" or "hydrocarbon oil" refers to oil mainly containing hydrogen and carbon atoms and possibly oxygen, nitrogen, sulfur and/or phosphorus atoms. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of silicone oils that may be useful in the present invention include nonvolatile silicone oils such as polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Other representative examples of silicone oils that may be useful in the present invention include volatile silicone oils such as linear or cyclic silicone oils, especially those with a viscosity ÿ centistokes (8×10-6 m 2/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of fluoro oils that may be suitable for use in the present invention include volatile fluro oils such as nonafluoromethoxybutane and perfluoro-methylcyclopentane.

The amount of the organic solvent/compound present in the compositions of the present invention can range from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 2% to about 6%, by weight, including all ranges and subranges there-between, relative to the total weight of the composition.

In some embodiments, the amount of the organic solvent/compound present in the compositions of the present invention is at about 2%, about 2.5%, about 3%, about 3.5%, about 4%, about 4.5%, about 5%, about 5.5% or about 6% by weight, including all ranges and subranges there-between, relative to the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include volatile organic solvents such as C2 to C4 monoalcohols, such as ethanol, isopropyl alcohol, butanol, polyols such as C2-C6 glycols e.g., propylene glycol, butylene glycol, pentylene glycol, hexylene glycol, glycerol, isododecane, volatile polyol ethers, volatile glycol ethers, acetone, propylene carbonate, benzyl alcohol, and mixtures thereof. In certain embodiments, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

Other preferred examples of organic solvents/compounds include nonvolatile organic solvents such as hydrocarbons such as straight chain hydrocarbons, nonvolatile silicone oils, mineral oil, polybutene, hydrogenated polyisobutene, hydrogenated polydecene, polydecene, squalene, petrolatum, isoparaffins, nonvolatile glycol ethers, and mixtures, thereof.

In certain embodiments, it is preferred that the amount of nonvolatile organic solvent/compound does not exceed 40% by weight, relative to the weight of the composition of the present invention.

In other certain embodiments, it is preferred that the amount of nonvolatile organic solvent/compound does not exceed 20% by weight, relative to the weight of the composition of the present invention.

In yet other certain embodiments, it is preferred that the amount of nonvolatile organic solvent/compound does not exceed 10% by weight, relative to the weight of the composition of the present invention.

In preferred embodiments of the present invention, the at least one organic solvent is chosen from ethanol, glycol ether, for example, dipropylene glycol n-butyl ether, known under the tradename of DOWANOL DPnB, isododecane, mineral oil, propylene glycol, pentylene glycol, hexylene glycol, glycerol, and mixtures thereof.

In certain embodiments of the present invention, the at least one organic solvent is chosen from ethanol.

The organic solvents may also comprise the solvent of the dispersion medium employed to disperse the latex polymers and silicone organic polymer compound of the present invention.

In yet some other embodiments, water that is not added as a separate ingredient, by itself, into the compositions of the present invention, such that water is present in the compositions of the present invention when it accompanies one or more ingredients of a raw material that is added into the composition invention.

Water

The compositions of the present invention contain water. Water can be present in the amount of about 95%, 90%, 80%, 70%, 60%, 50%, 40%, 30%, 20%, 10%, 5% by weight or less, relative the total weight of the compositions. Additionally, water can be present in the compositions of the present invention in the amount of from about 20% to about 95% by weight, or from about 50% to about 90% by weight, or from about 60% to about 80% by weight, relative to the weight of the compositions.

In other embodiments, water can be present in the compositions of the present invention in the amount of at least about 95%, 90%, 80%, 70%, 60%, 50%, 40%, 30%, 20%, 10%, 5% by weight or less, relative to the total weight of the compositions.

The oxidizing composition that is to be combined with the color base composition of the present invention may be in the form of a powder, gel, liquid, foam, lotion, cream, mousse, and emulsion.

The oxidizing composition of the present invention my contain at least one fatty substance chosen from oils, waxes and oil gellants. Thus, the total amount of fatty substances in the combination or mixture of the color base and oxidizing compositions of the present invention may range from about 10% to about 80% by weight, or such as from about 20% to about 60% by weight, or such as from about 20% to about 40% by weight, or such as from about 20% to about 30% by weight, based on the total weight of the composition.

pH

In some embodiments, the pH of the color base composition is greater than or equal to 7 and may range from about 7.1 to about 12, or such as from about 7.5 to about 11, or such as from about 7.5 to about 10 or such as from about 7.5 to about 9, or such as from about 9 to about 11.

In other embodiments, the pH of the color base composition of the present invention is less than 7 and can range from about 2 to 6.9, or such as from about 2 to about 6.8 or such as from about 3 to about 6.5 or such as from about 4 to about 6.5 or such as from about 4 to about 6.

The pH of the color base composition may be adjusted to the desired value using the neutralizing agents of the present invention and/or acidifying or basifying agents that are well known in the cosmetic arts.

The pH of the oxidizing composition can range from about 2 to about 12, such as from about 6 to about 11, and it may be adjusted to the desired value using acidifying/alkalizing agents that are well known in the art. In certain embodiments, the pH of the oxidizing composition is below 7.

The pH of the composition resulting from mixing together the color base composition and the oxidizing composition can be at least 6.5, and may range from about 6.5 to about 11, such as from about 6.8 to about 11, or from about 7 to about 11, or from about 8 to about 11, or from about 9.5 to about 11, or from about 9 to about 11, or from about 10 to about 11.

All numbers expressing pH values are to be understood as being modified in all instances by the term "about" which encompasses up to +3%.

According to at least one embodiment, the color base compositions and compositions comprising the color base composition and the oxidizing composition of the present invention are substantially free of ammonia.

In some embodiments, the color base composition can have a pH below 7, such as at about 6.5, about 6.6, about 6.7, about 6.8, about 6.9.

In other embodiments, the color base composition can have a pH above 7, such as at about 7.5, about 8, about 8.5, about 9, about 9.5, about 10, about 10.5.

The color base composition of the present disclosure is can be in the form of a gel, a gel cream, an emulsion, for example, oil-in-water emulsion and water-in-oil emulsion.

In some embodiments, the color base composition of the present disclosure is in the form of a gel or gel cream.

In other embodiments, the color base composition of the present disclosure is in the form of an oil-in-water emulsion.

The color base and oxidizing compositions of the present invention may further comprise at least one auxiliary agent suitable for use in cosmetic compositions. The auxiliary agent may include, but is not limited to thickening agents and rheology modifying polymers other than the acrylic polymers described above, cationic polymers, film forming non latex polymers, humectants and moisturizing agents, emulsifying agents other than those that fall under the above-described fatty substances, fillers, structuring agents, propellants, anionic surfactants, cationic surfactants, amphoteric surfactants, shine agents, and conditioning agents.

Thickening agents and rheology modifying polymers other than the above-described acrylic polymers may be chosen from polymeric thickeners and non-polymeric thickeners. The polymeric thickener can be chosen from ionic or non-ionic, associative or non-associative polymers. Exemplary polymeric thickeners include various native gums. Representative non-polymeric thickening agents include oxyethylenated molecules and especially ethoxylated alkyl or acyl derivatives of polyols. These polymers can be modified physically or chemically.

The at least one thickening agent may be employed in the compositions of the present invention in an amount of from greater than 0% to about 15% by weight, preferably from about 0.1% to about 10% by weight, and more preferably from about 1% to about 5% by weight, based on the total weight of the compositions of the present invention.

The compositions according to the present invention can also comprise at least one cationic polymer.

The cationic polymer may be chosen from cationic associative polymers comprising, in their structure, a pendent or terminal hydrophobic chain, for example of alkyl or alkenyl type, containing from 10 to 30 carbon atoms.

The at least one cationic polymer of the compositions can also be chosen from, for example:

(1) homopolymers and copolymers derived from acrylic or methacrylic esters or amides, examples of which are:

copolymers of acrylamide and of dimethylaminoethyl acrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in EP 80 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or acrylate copolymers, such as the products sold under the name GAFQUAT by the company ISP, for instance GAFQUAT 734 or GAFQUAT 755, or alternatively the products known as COPOLYMER 845, 958 and 937, dimethylaminoethyl acrylate/vinylcaprolactam/vinyl pyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, quaternized vinylpyrrolidone/dimethylaminopropylmethacrylamide copolymers such as the product sold under the name GAFQUAT HS 100 by the company ISP, and cross-linked polymers of methacryloyloxy(C1-C4)alkyltri(C1-C4)alkylammonium salts such as the polymers obtained by homopolymerization of dimethylaminoethyl acrylate quaternized with methyl chloride, or by copolymerization of acrylamide with dimethylaminoethyl acrylate quaternized with methyl chloride, the homo- or copolymerization being followed by crosslinking with a compound containing olefinic unsaturation, such as methylenebisacrylamide. In at least one embodiment, a crosslinked acrylamide/methacryloyloxyethyltrimethylammonium chloride copolymer (20/80 by weight) in the form of a dispersion containing 50% by weight of the copolymer in mineral oil can be used. This dispersion is sold under the name SALCARE® SC 92 by the company Ciba. In some embodiments, a crosslinked methacryloyloxyethyltrimethylammonium chloride homopolymer containing about 50% by weight of the homopolymer in mineral oil or in a liquid ester can be used. These dispersions are sold under the names SALCARE® SC 95 and SALCARE® SC 96 by the company Ciba.

Other examples are cellulose ether derivatives comprising quaternary ammonium groups, such as the polymers sold under the names JR (JR 400, JR 125, JR 30M) or LR (LR 400, LR 30M) by the company Union Carbide Corporation.

(2) copolymers of cellulose or cellulose derivatives grafted with a water-soluble quaternary ammonium monomer, such as hydroxymethyl-, hydroxyethyl- or hydroxypropylcelluloses grafted, for instance, with a methacryloylethyltrimethylammonium, methacrylamidopropyltrimethylammonium or dimethyldiallylammonium salt. These are sold under the name CELQUAT L 200 and CELQUAT H 100 by the company National Starch.

(3) non-cellulose cationic polysaccharides, such as guar gums containing trialkylammonium cationic groups. Such products are sold, for example, under the trade names JAGUAR C135, JAGUAR C15, JAGUAR C17 and JAGUAR C162 by the company Meyhall.

(4) polymers of piperazinyl units and of divalent alkylene or hydroxyalkylene radicals.

(5) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 to 0.35 mol per amine group of the polyamino amide; these polyamino amides can be alkylated or, if they contain at least one tertiary amine function, they can be quaternized. Exemplary mention may be made of the adipic acid/dimethylaminohydroxypropyl/ diethylenetriamine polymers sold under the name CAR-TARETINE F, F4 or F8 by the company Sandoz.

(6) the polymers obtained by reaction of at least one polyalkylene polyamine containing two primary amine groups and at least one secondary amine group with a dicarboxylic acid chosen from diglycolic acid and saturated C3-C8 aliphatic dicarboxylic acids. The molar ratio between the polyalkylene polyamine and the dicarboxylic acid ranges from 0.8:1 to 1.4:1; the polyamino amide resulting therefrom is reacted with epichlorohydrin in a molar ratio of epichlorohydrin relative to the secondary amine group of the polyamino amide ranging from 0.5:1 to 1.8:1. Polymers of this type are sold, for example, under the name HERCO-SETT 57, PD 170 or DELSETTE 101 by the company Hercules.

(7) cyclopolymers of alkyldiallylamine and of dialkyldiallylammonium, such as for example: dimethyldiallylammonium chloride homopolymer sold under the name MERQUAT® 100 and MERQUAT® 280 by the company Nalco (and its homologues of low weight-average molecular mass) and the copolymers of diallyldimethylammonium chloride and of acrylamide, sold under the name MERQUAT® 550.

(8) quaternary diammonium polymers.

(9) polyquaternary ammonium polymers; examples that may be mentioned include the products MIRAPOL A 15, MIRAPOL AD1, MIRAPOL AZ1 and MIRAPOL 175 sold by the company Miranol.

(10) quaternary polymers of vinylpyrrolidone and of vinylimidazole, for instance the products sold under the names LUVIQUAT FC 905, FC 550 and FC 370 by the company BASF.

(11) vinylamide homopolymers or copolymers, such as partially hydrolysed vinylamide homopolymers such as poly (vinylamine/vinylamide)s.

(12) cationic polyurethane derivatives, for example those of elastic nature formed from the reaction:

(a1) of at least one cationic unit resulting from at least one tertiary or quaternary amine bearing at least two reactive functions containing labile hydrogen, (a2) of at least one mixture of at least two different nonionic units bearing at least two reactive functions containing labile hydrogen, for instance chosen from hydroxyl groups, primary or secondary amine groups, and thiol groups, and (b) of at least one compound comprising at least two isocyanate functions.

(13) Other cationic polymers that may be used in the context of the disclosure include, for example, cationic proteins or cationic protein hydrolysates, polyalkyleneimines, such as polyethyleneimines, polymers containing vinylpyridine or vinylpyridinium units, and chitin derivatives.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5 to about 10% by weight, and more preferably from about 1 to about 5% by weight, based on the total weight of the compositions of the present invention.

The compositions of the present invention according to the disclosure can also comprise at least one additive used conventionally in compositions for application onto hair.

"Additive" means a substance that is added, different from the compounds already mentioned.

As examples of additives that can be used, non-limiting mentions can be made of antioxidants or reducing agents, penetrating agents, sequestering agents, perfumes, buffers, dispersants, ceramides, sunscreen agents, preservatives, opacifiers, and antistatic agents.

The color base and oxidizing compositions of the present invention according to the disclosure can be in various forms, such as in the form of liquids, creams, liquid-gels, liquid-creams, gels, lotions or pastes.

Method of Use

The color base compositions of the present invention are capable of being mixed or combined with a composition containing at least oxidizing agent ("oxidizing composition"). The combination of the color base composition and the oxidizing composition results in a final mixture or a ready to use composition which may also be called a composition for altering the color of hair.

The term "combined" and all variations of this term as used herein refers to contacting or mixing or reconstituting or dissolving or dispersing or blending or shaking the color base composition with the oxidizing composition. It can also mean introducing the color base composition to the oxidizing composition. It may also mean placing the color base composition in the same vessel or container as the oxidizing composition.

Thus, the process of altering the color of hair in accordance with the invention comprises applying a composition comprising the color base composition and the oxidizing composition of the present invention onto hair. Said composition that is applied onto hair is formed by mixing the color base composition with the oxidizing composition.

The color base composition can be mixed or combined with the oxidizing composition in a ratio by weight of from about 1:1 to about 1:10, such as from about 1:1 to about 1:4, preferably from about 1:1 to about 1:3, or preferably from about 1:1 to about 1:2.

Upon application of the composition comprising the color base composition and the oxidizing composition and after a resting time (leave-on time) on the keratin fibers, for example, ranging from about 1 to about 60 minutes, such as from about 5 to about 45 minutes, or such as from about 5 to about 20 minutes, or such as from about 10 to about 20 minutes, or such as of about 20 minutes, the keratin fibers are rinsed, optionally washed with shampoo, rinsed again, optionally washed with a hair conditioning composition, and rinsed again, then dried. The shampoo and hair conditioning composition can be any conventional hair shampoo and conditioner products.

In addition, independently of the embodiment use, the mixture or composition present on the fibers or hair (resulting from the extemporaneous mixing of the compositions, or from the successive application of the cosmetic and oxidizing compositions) is left in place for a time, generally, from about 1 to about 60 minutes, such as from about 5 to about 45 minutes, or such as from about 5 to about 20 minutes, or such as from about 10 to about 20 minutes, or such as of about 20 minutes.

The temperature during the process of altering the color of hair is between room temperature and 80° C. and preferably, between room temperature and 60° C.

It has been surprisingly discovered that association of ingredients in the color base composition of the invention, when combined with the oxidizing composition of the present invention, produced a final mixture or a composition with a non-drip consistency that is still easy to spread on keratin fibers, such as hair.

It has also been discovered that the application of the final mixture or composition onto the fibers results in satisfactory degree of color deposit and desirable shade formation coloring. At the same time, lower amounts of the oxidizing agent and/or lower amounts of oxidative dye precursors and dye compounds compared to the amounts of dyes in conventional dyeing compositions can be contemplated.

The coloring obtained on hair using the compositions and process of the present disclosure may also be durable or wash/fade resistant.

As used herein, the process and composition disclosed herein may be used on the hair that has not been previously artificially dyed or pigmented.

As used herein, the process and composition disclosed herein may be also used on the hair that has been previously artificially dyed or pigmented.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The examples that follow serve to illustrate embodiments of the present disclosure without, however, being limiting in nature.

EXAMPLES

The following Examples are intended to be non-restrictive and explanatory only, with the scope of the invention being defined by the claims.

The ingredient amounts/concentrations in the compositions/formulas described below are expressed in % by weight, relative to or based on the total weight of the composition/formula.

Example 1: Inventive Formulas

| INCI US | FORMULA A pH 10.15 | FORMULA B pH 10.75 |
|---|---|---|
| AMINOMETHYL PROPANOL | 0.3 | 0.3 |
| ERYTHORBIC ACID | 0.3 | 0.3 |
| SODIUM METABISULFITE | 0.5 | 0.5 |
| ETHANOLAMINE | 4 | 4 |
| EDTA | 0.2 | 0.2 |
| TOLUENE-2,5-DIAMINE (and) THIOGLYCERIN | 0.08 | — |
| 2-METHYL-5-HYDROXYETHYLAMINOPHENOL | 0.56 | — |
| 4-AMINO-3-NITROPHENOL | — | 0.4 |
| 3-NITRO-P-HYDROXYETHYLAMINOPHENOL | — | 0.3 |
| 4-AMINO-2-HYDROXYTOLUENE | 0.128 | — |
| HC RED NO. 3 | — | 0.6 |
| HC YELLOW NO. 9 | — | 0.2 |
| 6-HYDROXYINDOLE | 0.0184 | — |
| RESORCINOL | 0.104 | — |
| p-AMINOPHENOL (and) SODIUM METABISULFITE | 0.496 | — |
| MICA (and) TITANIUM DIOXIDE | — | — |
| XANTHAN GUM | 1 | 1 |
| CARBOMER | 6 | 6 |
| ACRYLATES COPOLYMER (28%) IN WATER ACULYN 33 ™ (DOW CHEMICAL) | 3 | 3 |
| ACRYLATES/HYDROXYESTERS ACRYLATES COPOLYMER (47.5 TO 48.5%) IN WATER ACUDYNE 180 (DOW CHEMICAL) | 2.6 | 2.6 |
| POLYQUATERNIUM-5 MERQUAT 5 POLYMER (NALCO/LUBRIZOL) | 0.2 | 0.2 |
| POLYQUATERNIUM-39 (10.2 TO 11.5%) IN WATER MERQUAT 3330PR POLYMER (NALCO/LUBRIZOL) | 1 | 1 |
| DIPROPYLENE GLYCOL | 3 | 3 |
| PROPYLENE GLYCOL | 4 | 4 |
| WATER | 72.5136 | 72.4 |

Process of Making the Inventive Formulas

Formula A (with Oxidative Dyes); Gel Formula

| Phase | INCI Name | % wt/wt |
|---|---|---|
| A | Deionized Water | 35.96 |
| A | Xanthan gum | 1.00 |
| A | Propylene Glycol | 4.00 |
| A | Dipropylene Glycol | 3.00 |
| A | Polyquaterinum-5 | 0.20 |
| A | Carbomer (4% solution) | 6.00 |
| A | Polyquaterinum-39 | 1.00 |
| A | Monoethanolamine | 4.00 |
| A | Sodium Metabisulfite | 0.50 |
| A | Erythorbic Acid | 0.30 |
| A | EDTA | 0.20 |
| A | Toluene-2,5-Diamine | 0.08 |
| A | p-Aminophenol | 0.50 |
| A | Resorcinol | 0.10 |
| A | 2-Methyl-5-Hydroxyethylaminophenol | 0.56 |
| A | 6-Hydroxyindole | 0.018 |
| A | 4-Amino-2-Hydroxytoluene | 0.128 |
| B | Deionized Water | 36.56 |
| B | Amino methyl propanol | 0.30 |
| B | Acrylates copolymer (28%) in water | 3.00 |
| B | Acrylates/hydroxyesters acrylates copolymer (47.5 TO 48.5%) in water | 2.60 |

The following procedure was followed in making Formula A:

Phase A
1. Add Xanthan gum to 50% Deionized Water. Mix until Xanthan gum is fully dissolved
2. Add Propylene Glycol. Mix for 10 minutes
3. Add Dipropylene Glycol. Mix for 10 minutes
4. Add Polyquaterinum-39. Mix for 10 minutes
5. Add Polyquaterinum-5. Mix for 10 minutes
6. Add dyes, Antioxidants, EDTA and monoethanolamine. Mix for 10 minutes
7. Add Carbomer & mix until full dissolved Phase B
1. Add Acrylates copolymer & Acrylates/hydroxyesters acrylates copolymer to remainder of Deionized Water in separate beaker
2. Add Amino methyl propanol. Solution will be transparent. Mix until entire batch is transparent
3. Add Phase B to Phase A. Mix for 10 minutes
4. QS with Deionized Water Formula B (with Oxidative Dyes and Direct Dyes); Gel Formula

| Phase | INCI Name | % wt/wt |
|---|---|---|
| A | Deionized Water | 35.84 |
| A | Xantham gum | 1.00 |
| A | Propylene Glycol | 4.00 |
| A | Dipropylene Glycol | 3.00 |
| A | Polyquaterinum-5 | 0.20 |
| A | Carbomer (4% solution) | 6.00 |
| A | Polyquaterinum-39 | 1.00 |
| A | Monoethanolamine | 4.00 |
| A | Sodium Metabisulfite | 0.50 |
| A | Erythorbic Acid | 0.30 |
| A | EDTA | 0.20 |
| A | 3-NITRO-P-HYDROXYETHYLAMINOPHENOL | 0.30 |
| A | 4-AMINO-3-NITROPHENOL | 0.40 |
| A | HC YELLOW NO. 9 | 0.20 |
| A | HC RED NO. 3 | 0.60 |
| B | Deionized Water | 36.56 |
| B | Amino methyl propanol | 0.30 |
| B | Acrylates copolymer (28%) in water | 3.00 |
| B | Acrylates/hydroxyesters acrylates copolymer (47.5 TO 48.5%) in water | 2.60 |

The following procedure was followed in making Formula B:

Phase A
1. Add Xanthan gum to 50% Deionized Water. Mix until Xanthan gum is fully dissolved
2. Add Propylene Glycol. Mix for 10 minutes
3. Add Dipropylene Glycol. Mix for 10 minutes
4. Add Polyquaterinum-39. Mix for 10 minutes
5. Add Polyquaterinum-5. Mix for 10 minutes
6. Add dyes, Antioxidants, EDTA and monoethanolamine. Mix for 10 minutes
7. Add Carbomer & mix until full dissolved.

Phase B
1. Add Acrylates copolymer & Acrylates/hydroxyesters acrylates copolymer to remainder of Deionized Water in separate beaker
2. Add Amino methyl propanol. Solution will be transparent. Mix until entire batch is transparent
3. Add Phase B to Phase A. Mix for 10 minutes
4. QS with Deionized Water.

if an emulsion color base composition of the invention is desired, other ingredients including mineral oil, nonionic surfactants, emulsifiers, or waxes can be added (some water is replaced with these ingredients).

Oxidizing Composition (also called developer composition which is to be mixed with each of the inventive and comparative formulas to form a final mixture or composition that is applied onto hair)

| INCI US | (10 volume developer)* % by weight |
|---|---|
| HYDROGEN PEROXIDE (50% activity in water) | 6 |
| Other ingredients: water, glycerin, cetearyl alcohol, ceteareth-25, pentasodium pentetate, tetrasodium pyrophosphate, trideceth-2 carboxaminde MEA, sodium stannate | |

*A 20 volume developer containing 12% (50% activity in water) by weight relative to the total weight of the developer composition may also be used Example Inventive and Comparative Formulas

| INCI US | inventive formula A | comparative formula with one latex polymer C pH 10.26 | comparative formula with one latex polymer D pH 10.35 |
|---|---|---|---|
| AMINOMETHYL PROPANOL | 0.3 | 0.3 | 0.3 |
| ERYTHORBIC ACID | 0.3 | 0.3 | 0.3 |
| SODIUM METABISULFITE | 0.5 | 0.5 | 0.5 |
| ETHANOLAMINE | 4 | 4 | 4 |
| EDTA | 0.2 | 0.2 | 0.2 |
| TOLUENE-2,5-DIAMINE (and) THIOGLYCERIN | 0.08 | 0.08 | 0.08 |
| 2-METHYL-5-HYDROXYETHYLAMINOPHENOL | 0.56 | 0.56 | 0.56 |
| 4-AMINO-2-HYDROXYTOLUENE | 0.128 | 0.128 | 0.128 |
| 6-HYDROXYINDOLE | 0.0184 | 0.0184 | 0.0184 |
| RESORCINOL | 0.104 | 0.104 | 0.104 |
| p-AMINOPHENOL (and) SODIUM METABISULFITE | 0.496 | 0.496 | 0.496 |
| XANTHAN GUM | 1 | 1 | 1 |
| CARBOMER | 6 | 6 | 6 |
| ACRYLATES COPOLYMER (28%) IN WATER ACULYN 33 ™ (DOW CHEMICAL) | 3 | 3 | — |

-continued

| INCI US | inventive formula A | comparative formula with one latex polymer C pH 10.26 | comparative formula with one latex polymer D pH 10.35 |
|---|---|---|---|
| ACRYLATES/HYDROXYESTERS ACRYLATES COPOLYMER (47.5 TO 48.5%) IN WATER ACUDYNE 180 (DOW CHEMICAL) | 2.6 | — | 2.6 |
| POLYQUATERNIUM-5 MERQUAT 5 POLYMER (NALCO/LUBRIZOL) | 0.2 | 0.2 | 0.2 |
| POLYQUATERNIUM-39 (10.2 TO 11.5%) IN WATER MERQUAT 3330PR POLYMER (NALCO/LUBRIZOL) | 1 | 1 | 1 |
| DIPROPYLENE GLYCOL | 3 | 3 | 3 |
| PROPYLENE GLYCOL | 4 | 4 | 4 |
| WATER | 72.5136 | 75.1136 | 75.5136 |

Example 3: Inventive and Comparative Formulas

| INCI US | Inventive A | Comparative without latex polymer A1 |
|---|---|---|
| AMINOMETHYL PROPANOL | 0.3 | |
| ERYTHORBIC ACID | 0.3 | 0.3 |
| SODIUM METABISULFITE | 0.5 | 0.5 |
| ETHANOLAMINE | 4 | 4 |
| EDTA | 0.2 | 0.2 |
| TOLUENE-2,5-DIAMINE (and) THIOGLYCERIN | 0.08 | 0.08 |
| 2-METHYL-5-HYDROXYETHYLAMINOPHENOL | 0.56 | 0.56 |
| 4-AMINO-2-HYDROXYTOLUENE | 0.128 | 0.128 |
| 6-HYDROXYINDOLE | 0.0184 | 0.0184 |
| RESORCINOL | 0.104 | 0.104 |
| p-AMINOPHENOL (and) SODIUM METABISULFITE | 0.496 | 0.496 |
| XANTHAN GUM | 1 | 1 |
| CARBOMER (98%) IN WATER CARBOPOL 980 POLYMER (LUBRIZOL) | 6 | 6 |
| ACRYLATES COPOLYMER (28%) IN WATER ACULYN 33 ™ (DOW CHEMICAL) | 3 | — |
| ACRYLATES/HYDROXYESTERS ACRYLATES COPOLYMER (47.5 TO 48.5%) IN WATER ACUDYNE 180 (DOW CHEMICAL) | 2.6 | — |
| POLYQUATERNIUM-5 MERQUAT 5 POLYMER (NALCO/LUBRIZOL) | 0.2 | 0.2 |
| POLYQUATERNIUM-39 (10.2 TO 11.5%) IN WATER MERQUAT 3330PR POLYMER (NALCO/LUBRIZOL) | 1 | 1 |
| DIPROPYLENE GLYCOL | 3 | 3 |
| PROPYLENE GLYCOL | 4 | 4 |
| WATER | 72.5136 | 78.4136 |

Procedure for Dyeing Hair and Colorimetric Measurements

Each of the inventive and comparative formulas was mixed with the indicated oxidizing compositions and the resulting mixtures of compositions were then used on hair according to the following general procedure:

10 g of the base composition was mixed with 10 g of the oxidizing composition (1:1 ratio);

the resulting mixture or composition was applied onto hair swatches and left to stand on the hair from about 20-30 minutes;

the hair swatches were then washed with shampoo, rinsed and then dried.

If desired, the color base composition can be mixed with the oxidizing composition in a 1:2 ratio or a 1:3 ratio or a 1:4 ratio. Unless specified otherwise, all ratios of cosmetic composition to oxidizing composition in the examples presented are 1:1 ratios.

The resulting mixtures or compositions of the invention had pH values of greater than 7. Formulas A and B had a mix pH of 10.05 and 10.15, respectively. The resulting mixtures or compositions obtained from comparative Formulas C and D, had a mix pH of 9.99 and 10.02, respectively.

It was found that before mixing with an oxidizing composition, the inventive color base compositions had an excellent, non-drip consistency. This consistency remained even after the inventive color base compositions were mixed with the oxidizing compositions.

For measuring the degree of change in the color of hair (e.g. degree of lightening/lifting color or color deposit) after treating the hair, the color of each swatch was measured with a Minolta CM2600d spectrocolorimeter (specular components included, 10 degrees angle, illuminant D65) in the CIEL*a*b* system.

The L parameter L was measured. L* represents the intensity of the color. The greater the value of L, the lighter or less intense the color. Conversely, the lower the value of L, the darker or more intense the color (this can also indicate greater color deposit when the composition contains colorants).

ΔL or the difference between the L value for the treated hair versus the L value for the control hair swatch can also be measured. ΔL represents a change in the value of L: the more negative the ΔL value is, the darker the color that is deposited on the hair: ΔL=Lt (treated hair)−Lc (control hair).

TABLE 1

COLORIMETRIC MEASUREMENTS FOR COLOR DEPOSIT ON HAIR SWATCHES (inventive formula containing two latex polymers versus formulas containing only one latex polymer, formulas containing no latex polymer, and a commercial formula)

| Product | Shade | 90% Gray Hair Type | L* |
|---|---|---|---|
| No dye treatment (CONTROL 1) on unpermed hair | | | 57.65 |
| Commercial formula* (CONTROL 2) | 7C | Unpermed | 24.05 |
| FORMULA A 2 Neutralized Latex polymers | 7C | Unpermed | 15.23 |
| FORMULA C 1 Neutralized Latex polymer (ACULYN 33) | 7C | Unpermed | 24.36 |
| FORMULA D 1 Neutralized Latex polymer (ACUDYNE 180 Polymer) | 7C | Unpermed | 23.89 |
| FORMULA A1 No Latex polymer (CONTROL 3) | 7C | Unpermed | 23.86 |
| No dye treatment (CONTROL 1) on upermed hair | | | 57.79 |
| Commercial formula* (CONTROL 2) | 7C | Permed | 22.36 |
| FORMULA A 2 Neutralized Latex polymers | 7C | Permed | 15.47 |
| FORMULA C 1 Neutralized Latex polymer (ACULYNTM 33) | 7C | Permed | 21.89 |
| FORMULA D 1 Neutralized Latex polymer (ACUDYNE 180 Polymer) | 7C | Permed | 21.87 |
| FORMULA A1 No Latex polymer (CONTROL 3) | 7C | Permed | 19.15 |

*Commercial formula did not contain any latex polymers

From the table above, the L values for hair dyed with Control 3 formula, Control 2 formula & the formulas containing only one neutralized latex polymer were comparable which means that the use of these formulas on hair resulted in comparable degrees of color deposit for both permed & unpermed hair.

The L values for hair dyed with Control 3 formula, Control 2 formula & formulas containing only one neutralized latex polymer were significantly higher than the L values for hair dyed with the inventive formula; a higher L value is indicative of a lighter color or less color deposit. Thus, the use of the inventive formula on hair resulted in significantly greater degrees of color deposit in both permed & unpermed hair.

Example 3: Inventive and Comparative Formulas

| INCI US | Inventive formula A* | Comparative formula with 2 different latex polymers A2**, pH 10.23 |
|---|---|---|
| AMINOMETHYL PROPANOL | 0.3 | 0.3 |
| ERYTHORBIC ACID | 0.3 | 0.3 |
| SODIUM METABISULFITE | 0.5 | 0.5 |
| ETHANOLAMINE | 4 | 4 |
| EDTA | 0.2 | 0.2 |
| TOLUENE-2,5-DIAMINE (and) THIOGLYCERIN | 0.08 | 0.08 |
| 2-METHYL-5-HYDROXYETHYLAMINOPHENOL | 0.56 | 0.56 |
| 4-AMINO-2-HYDROXYTOLUENE | 0.128 | 0.128 |
| 6-HYDROXYINDOLE | 0.0184 | 0.0184 |
| RESORCINOL | 0.104 | 0.104 |
| p-AMINOPHENOL (and) SODIUM METABISULFITE | 0.496 | 0.496 |
| XANTHAN GUM | 1 | 1 |
| CARBOMER | 6 | 6 |
| ACRYLATES COPOLYMER (28%) IN WATER ACULYN 33 ™ (DOW CHEMICAL) | 3 | — |
| ACRYLATES/HYDROXYESTERS ACRYLATES COPOLYMER (47.5 TO 48.5%) IN WATER ACUDYNE 180 (DOW CHEMICAL) | 2.6 | — |
| ACRYLATES COPOLYMER DAITOSOL 5000 AD (50%) IN WATER (DAITO KASEI KOGYO) | — | 2.6 |
| ACRYLATES COPOLYMER (55%) IN WATER BALANCE CR (AZKO NOBEL) | — | 3 |
| POLYQUATERNIUM-5 MERQUAT 5 POLYMER (NALCO/LUBRIZOL) | 0.2 | 0.2 |
| POLYQUATERNIUM-39 (10.2 TO 11.5%) IN WATER MERQUAT 3330PR POLYMER (NALCO/LUBRIZOL) | 1 | 1 |
| DIPROPYLENE GLYCOL | 3 | 3 |
| PROPYLENE GLYCOL | 4 | 4 |
| WATER | 72.5136 | 72.5136 |

*inventive formula = combined amount of active latex polymers ranges from 2.07% to 2.101%
**comparative formula contained two different latex polymers; mix pH with oxidizing composition was 10.10; combined amount of active latex polymers is 2.95%

TABLE 2

COLORIMETRIC MEASUREMENTS FOR COLOR DEPOSIT ON HAIR SWATCHES

| Product | Shade | 90% Gray Hair Type | L* |
|---|---|---|---|
| No dye treatment (CONTROL 1) on unpermed hair | | | |
| Commercial formula* (CONTROL 2) | 7C | Unpermed | 24.05 |
| FORMULA A 2 Neutralized Latex polymers | 7C | Unpermed | 15.23 |
| FORMULA A2 2 Neutralized Latex polymers (DAITOSOL 5000 & BALANCED CR) | 7C | Unpermed | 23.15 |
| No dye treatment (CONTROL 1) on permed hair | | | |
| Commercial formula* (CONTROL 2) | 7C | Permed | 22.36 |
| FORMULA A 2 Neutralized Latex polymers | 7C | Permed | 15.47 |
| FORMULA A2 2 Neutralized Latex polymers (DAITOSOL 5000 & BALANCED CR) | 7C | Permed | 21.95 |

*comparative formulas contained two different latex polymers
From the table above, the L values for hair dyed with Control 2 formula & the formula (Formula A2) containing two neutralized latex polymers different from those used in the inventive formulas were similar. This means that the use of these formulas on hair resulted in comparable degrees of color deposit for both permed & unpermed hair.

The L values for hair dyed with Control 2 formula & Formula A2 were significantly higher than the L values for hair dyed with the inventive formula. Thus, the use of the inventive formula on hair resulted in significantly greater degrees of color deposit in both permed & unpermed hair.

Example 4: Stability Studies

The inventive formulas were tested for stability in a controlled environment chamber for 12 weeks at room temperature and at 45° C. The compositions showed no phase separation and maintained their gel-like or cream-like structure. Stability was also independent of the presence of oxidation dyes and oil.

The foregoing description illustrates and describes the present invention. Additionally, the disclosure shows and describes only the preferred embodiments of the invention, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:

1. A color base composition comprising:
   (a) at least two latex polymers independently selected from acrylate latex polymers and polyurethane latex polymers;
   (b) at least one alkalizing agent;
   (c) at least one oxidative dye precursor;
   (d) at least one organic solvent; and
   (e) water;
   wherein the at least two latex polymers are partially or fully neutralized; and
   wherein the at least two latex polymers are present in a combined amount ranging from about 0.2% to less than 2.5% by weight, based on a dry weight basis, relative to the weight of the composition.

2. The color base composition of claim 1, wherein each of the at least two latex polymers is present in individual amounts ranging from about 0.1% to about 1.5% by weight, relative to the weight of the composition.

3. The color base composition of claim 2, wherein the at least one alkalizing agent is present in an amount ranging from about 1% to about 20% by weight, relative to the weight of the composition.

4. The color base composition of claim 3, wherein the at least one alkalizing agent is selected from alkali metal carbonates, alkali metal phosphates, organic amines, hydroxide base compounds, and mixtures thereof.

5. The color base composition of claim 4, wherein the at least one alkalizing agent is selected from aminomethyl propanol, aminomethyl propanediol, triisopropanol amine) sodium hydroxide, potassium hydroxide, ammonium hydroxide, dimethylstearylamine, dimethyl/tallowamine lysine, ornithine, arginine, monoethanolamine, triethanolamine, calcium hydroxide, calcium bicarbonate, sodium bicarbonate, and mixtures thereof.

6. The color base composition of claim 5, wherein the pH of the composition ranges from about 6.5 to about 11.

7. The color base composition of claim 6, wherein the at least one oxidative dye precursor is selected from ortho- and para-phenylenediamine oxidation bases, double bases, ortho- and para-aminophenols, heterocyclic bases, salts of addition of these compounds with an acid, meta-aminophenol, meta-phenylenediamine, meta-diphenol, naphthol couplers, heterocyclic couplers and acid salts thereof.

8. The color base composition of claim 7, wherein the at least one organic solvent is present in an amount of from about 1% to about 20% by weight, relative to the total weight of the composition.

9. The color base composition of claim 8, wherein the at least one organic solvent (c) is chosen from volatile and non-volatile organic solvents.

10. The color base composition of claim 9, wherein the at least one organic solvent is selected from ethanol, isopropyl alcohol, butanol, propylene glycol, butylene glycol, pentylene glycol, hexylene glycol, glycerol, isododecane, acetone, propylene carbonate, benzyl alcohol, mineral oil, polybutene, hydrogenated polyisobutene, hydrogenated polydecene, polydecene, squalene, petrolatum, ethylene glycol monomethyl ether, ethylene glycol monopropyl ether, ethylene glycol monobutyl ether, propylene glycol monomethyl ether, propylene glycol monopropyl ether, propylene glycol monobutyl ether, diethylene glycol monoethyl ether, diethylene glycol monobutyl ether, dipropylene glycol n-butyl ether, and mixtures thereof.

11. The color base composition of claim 9, wherein at least one latex polymer is a film-forming latex polymer.

12. The color base composition of claim 9, comprising at least two latex polymers selected from acrylate latex polymers.

13. The color base composition of claim 9, comprising at least two latex polymers selected from polyurethane latex polymers.

14. The color base composition of claim 9, comprising at least two latex polymers independently selected from acrylate latex polymers and polyurethane latex polymers.

15. The color base composition of claim 14, wherein the at least two latex polymers are selected from Acrylates copolymer, Acrylates/Hydroxyesters Acrylates Copolymer, Polyacrylate-2 Crosspolymer, Styrene/Acrylic copolymer, Acrylates/Ethylhexyl Acrylate Copolymer, aliphatic polyurethane, Polyurethane-34, Polyurethane-32, Polyurethane-35, Polyurethane-48, Polyurethane-1, Polycarbamyl Polyglycon Ester, and mixtures thereof.

16. The color base composition of claim 9, further comprising at least one auxiliary ingredient selected from direct dyes, pigments, oils other than the at least one organic solvent, waxes, thickening agents and rheology modifying polymers other than the acrylic polymers described above, cationic polymers, film forming non latex polymers, humectants and moisturizing agents, emulsifying agents other than those that fall under the above-described fatty substances, fillers, structuring agents, propellants, anionic surfactants, cationic surfactants, amphoteric surfactants, shine agents, and conditioning agents and mixtures thereof.

17. The color base composition of claim 16, wherein the at least one auxiliary ingredient is selected from waxes and wherein the waxes comprise C3-45 alkyldimethylsilyl polypropylsilsesquioxane wax.

18. The color base composition of claim 16, wherein the at least one auxiliary ingredient is selected from rheology modifiers and viscosity modifying/thickening agents, and wherein the rheology modifiers and viscosity modifying/thickening agents are selected from carbomers, cellulose-based thickeners, gums of microbial origin, gums derived from plant exudates, pectins, alginates, starches, crosslinked homopolymers of acrylic acid or of acrylamidopropanesulfonic acid, and mixtures thereof.

19. The color base composition of claim 9, wherein the color base composition is capable of being mixed with an oxidizing composition comprising at least one oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture.

20. The color base composition of claim 1, wherein the color base composition is capable of being combined with a composition comprising at least one oxidizing agent in order to form a composition for altering the color of hair.

21. A composition for altering the color of hair comprising:
   A. A color base composition comprising:
      (a) at least two latex polymers independently selected from acrylate latex polymers and polyurethane latex polymers;
      (b) at least one alkalizing agent;
      (c) at least one oxidative dye precursor;
      (d) at least one organic solvent; and
      (e) water;
      wherein the at least two latex polymers are partially or fully neutralized; and
      wherein the at least two latex polymers are present in a combined amount ranging from about 1% to about 2.2% by weight, based on a dry weight basis, relative to the weight of the composition; and
   B. an oxidizing composition containing at least one oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture.

22. The composition for altering the color of hair of claim 21, wherein the composition further comprises at least one auxiliary ingredient selected from direct dyes, pigments, oils other than the at least one organic solvent, waxes, surfactants, rheology modifiers and viscosity modifying/thickening agents, conditioning agents, sequestering agents, emulsifiers, humectants, plasticizers, coalescers, fillers, preserving agents, fragrances, antioxidants, wetting agents, spreading agents, dispersants, sunscreens, and mixtures thereof.

23. A color base composition comprising:
   (a) at least two latex polymers selected from Acrylates copolymer, Acrylates/Hydroxyesters Acrylates Copolymer, Polyacrylate-2 Crosspolymer, Styrene/Acrylic copolymer, Acrylates/Ethylhexyl Acrylate Copolymer, aliphatic polyurethane, Polyurethane-34, Polyurethane-34, Polyurethane-32, Polyurethane-35, Polyurethane-48, Polyurethane-1, Polycarbamyl Polyglycon Ester, and mixtures thereof;
   (b) at least one alkalizing agent;
   (c) at least one oxidative dye precursor;
   (d) at least one organic solvent; and
   (e) water;
   (f) optionally, at least one auxiliary ingredient selected from direct dyes, pigments, oils other than the at least one organic solvent, waxes, surfactants, rheology modifiers and viscosity modifying/thickening agents, conditioning agents, sequestering agents, emulsifiers, humectants, plasticizers, coalescers, fillers, preserving agents, fragrances, antioxidants, wetting agents, spreading agents, dispersants, sunscreens, and mixtures thereof;
   wherein the at least two latex polymers are partially or fully neutralized; and
   wherein the at least two latex polymers are present in a combined amount ranging from about 1% to about 2.3% by weight, based on a dry weight basis, relative to the weight of the composition.

24. A method of coloring hair, comprising contacting hair with a composition for altering the color of hair, the composition comprising:
   A. A color base composition comprising:
      (a) at least two latex polymers independently selected from acrylate latex polymers and polyurethane latex polymers;
      (b) at least one alkalizing agent;
      (c) at least one oxidative dye precursor;
      (d) at least one organic solvent; and
      (e) water;
      wherein the at least two latex polymers are partially or fully neutralized; and
      wherein the at least two latex polymers are present in a combined amount ranging from about 0.2% to about 2.5% by weight, based on a dry weight basis, relative to the weight of the composition; and
   B. an oxidizing composition containing at least one oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from water and a water/organic solvent mixture;
   wherein the color base composition (A) is capable of being combined with the oxidizing composition (B).

25. A method of making a color base composition comprising:
   A. combining:
      (i) at least two latex polymers independently selected from acrylate latex polymers and polyurethane latex polymers; and
      (ii) at least one neutralizing agent selected from alkali metal carbonates, alkali metal phosphates, organic amines, hydroxide base compounds, and mixtures thereof;
   B. mixing (i) and (ii) in order to form partially or fully neutralized latex polymers;
   C. combining:
      (a) the partially or fully neutralized latex polymers in B;
      (b) at least one alkalizing agent;
      (c) at least one oxidative dye precursor;
      (d) at least one organic solvent; and
      (e) water;
      wherein the at least two latex polymers are present in a combined amount ranging from about 0.2% to about 2.5% by weight, based on a dry weight basis, relative to the weight of the composition; and
   D. mixing (a) to (e), in order to form the color base composition.

26. A multi-compartment kit for altering the color of hair comprising:
   A. a first compartment containing color base composition comprising:
      (a) at least two latex polymers independently selected from acrylate latex polymers and polyurethane latex polymers;
      (b) at least one alkalizing agent;
      (c) at least one oxidative dye precursor;
      (d) at least one organic solvent; and
      (e) water;

wherein the at least two latex polymers are partially or fully neutralized; and wherein the at least two latex polymers are present in a combined amount ranging from about 0.2% to about 2.5% by weight, based on a dry weight basis, relative to the weight of the composition; and B. a second compartment containing an oxidizing composition comprising at least one oxidizing agent selected from peroxides, urea peroxide, alkali metal bromates, ferricyanides, peroxygenated salts, perborates, percarbonates, laccases, peroxidases, redox enzymes, and mixtures thereof, and a cosmetically acceptable solvent selected from selected from water and a water/organic solvent mixture.

* * * * *